US006840935B2

(12) United States Patent
Lee

(10) Patent No.: US 6,840,935 B2
(45) Date of Patent: Jan. 11, 2005

(54) GYNECOLOGICAL ABLATION PROCEDURE AND SYSTEM USING AN ABLATION NEEDLE

(75) Inventor: Bruce B. Lee, Carmel, CA (US)

(73) Assignee: BEKL Corporation, Carmel, CA (US)

( * ) Notice: Subject to any disclaimer, the term of this patent is extended or adjusted under 35 U.S.C. 154(b) by 0 days.

(21) Appl. No.: 09/920,425

(22) Filed: Jul. 31, 2001

(65) Prior Publication Data

US 2002/0022835 A1 Feb. 21, 2002

Related U.S. Application Data

(60) Provisional application No. 60/224,191, filed on Aug. 9, 2000.

(51) Int. Cl.[7] .............................................. A61B 18/18
(52) U.S. Cl. ........................ 606/34; 128/898; 600/439
(58) Field of Search ..................... 606/32–52; 128/898; 600/439

(56) References Cited

U.S. PATENT DOCUMENTS

| | | | | |
|---|---|---|---|---|
| 5,234,004 A | * | 8/1993 | Hascoet et al. ............. | 607/116 |
| 5,293,863 A | | 3/1994 | Zhu et al. .................... | 128/20 |
| 5,759,162 A | * | 6/1998 | Oppelt et al. ................ | 601/2 |
| 5,911,036 A | | 6/1999 | Wright et al. ................ | 395/94 |
| 5,935,123 A | * | 8/1999 | Edwards et al. ............. | 606/41 |
| 5,979,453 A | * | 11/1999 | Savage et al. .............. | 128/898 |
| 6,190,383 B1 | * | 2/2001 | Schmaltz et al. ........... | 606/170 |
| 6,212,433 B1 | * | 4/2001 | Behl .......................... | 128/898 |
| 6,217,518 B1 | * | 4/2001 | Holdaway et al. .......... | 600/443 |
| 6,254,601 B1 | * | 7/2001 | Burbank et al. ............ | 606/45 |
| 6,355,033 B1 | * | 3/2002 | Moorman et al. ........... | 606/33 |
| 6,575,969 B1 | * | 6/2003 | Rittman et al. ............. | 606/41 |

* cited by examiner

*Primary Examiner*—Michael Peffley
*Assistant Examiner*—Pete Vrettakos
(74) *Attorney, Agent, or Firm*—MacPherson Kwok Chen & Heid LLP; David S. Park

(57) ABSTRACT

A method for treating pelvic tumors, such as uterine leiomyomata, includes inserting an ablation apparatus into a pelvic region and positioning the ablation apparatus either proximate or into a pelvic tumor. The method further includes using a laparoscope and an imaging device, such as an ultrasound machine, to confirm the location of the pelvic tumor and placement of the ablation apparatus. Various ablation apparatuses may be used, including those with multiple needles or deployable arms that are inserted into the pelvic tumor and those without arms. The method further includes delivering electromagnetic energy or other energy through the ablation apparatus to the pelvic tumor to ablate the tumor. A surgical system for ablating pelvic tumors is also provided.

28 Claims, 3 Drawing Sheets

GYNECOLOGICAL ABLATION PROCEDURE AND SYSTEM USING AN ABLATION NEEDLE

This application claims benefits of Provisional Application 60/224,191, filed Aug. 9, 2000.

FIELD OF THE INVENTION

The present invention relates to a procedure and system for treating gynecological disorders. More particularly, the present invention relates to the treatment of pelvic tumors.

BACKGROUND OF THE INVENTION

Benign and malignant tumors can occur in the pelvis. For example, uterine leiomyomata, are muscle cell tumors that occur in 77% of women in the reproductive years. Although uterine leiomyomata rarely (0.1%) progress to cancer, these tumors can cause excessive menstrual bleeding, irregular bleeding, pregnancy loss, infertility, urinary frequency, and pelvic pressure or pain with sexual activity, menses, or daily activities. Women with uterine leiomyomata frequently incur surgical procedures (e.g., hysterectomy, dilatation and curettage, myomectomy, and hysteroscopy), medical and hormonal therapies, office visits, and a variety of radiologic procedures (e.g., ultrasounds, CAT scans, and MRIs), in an effort to treat these tumors. Uterine leiomyomata account for approximately 200,000 hysterectomies per year in the United States alone, at a direct cost of well over $2 billion. Hysterectomies carry a morbidity rate of 1%, with 2,000 deaths per year and 240,000 complications per year in North America.

Uterine leiomyomata are most often multiple, and may be subserosal (i.e., bulging externally from the uterus), intramural (i.e., growing entirely within the wall of the uterus), submucosal (i.e., hidden within the uterine cavity), or pedunculated (i.e., growing outward with a stalk-like base). Because patients may have multiple uterine leiomyomata at different locations, conservative surgeries may involve both an abdominal and a vaginal (hysteroscopic) approach, thereby necessitating two procedures.

Investigators have utilized a laser or bipolar cautery to perform myolysis or destruction of these tumors, although neither of these methods is performed in significant numbers today. These methods necessarily destroy normal overlying tissue in order to treat the underlying tumor. As a result, the integrity of the uterus is compromised, and harmful scar tissue (e.g., adhesions) may occur. Thus, there is a need for an improved method of treating benign and malignant pelvic tumors that does not damage the overlying tissue. Such an improved method could be used on women who wish to later conceive and subsequently deliver. There is also a need for a single method capable of treating all sizes of subserosal, intramural, submucuosal, and pedunculated tumors in all locations. A single method, which would relieve most or all symptoms of abdominal or pelvic pain/pressure, abnormal uterine bleeding, urinary frequency, infertility, and miscarriage, is also needed. In addition, it would be desirable for the method to be less invasive, cheaper, and safer than conventional methods of treating pelvic tumors, and also to allow for uterine preservation.

SUMMARY OF THE INVENTION

The present invention, also referred to as "the Halt procedure," is an innovative, outpatient procedure that utilizes electromagnetic energy to effectively ablate pelvic tumors. The invention employs an ablation device that uses radio-frequency (RF) energy to treat pelvic tumors, while sparing the surrounding normal tissue. Although the ablation device utilized in the present invention has FDA approval for ablation of soft tissue tumors, no known reports exist in the medical literature of the ablation device's application to uterine leiomyomata or other pelvic tumors. In addition, current results indicate that, compared to other conservative therapies, the present method is very effective. Thus far, the present invention has provided relief from all of the types of symptoms caused by pelvic tumors, such as uterine leiomyomata. Furthermore, the present invention is versatile, safe, and well-accepted by patients. Advantages of the present invention include a quick recovery time, typically no more than a week, and significant cost savings. More importantly, the present invention provides a practical and efficient way to achieve uterine conservation on an out-patient basis.

In accordance with one embodiment of the present invention, a method of treating a pelvic tumor includes inserting an ablation device into a pelvic region and positioning the ablation device proximate the pelvic tumor, using a laparoscope and an imaging device to confirm placement of the ablation apparatus. Various ablation devices may be used. For example, the ablation device may include no arms, a plurality of deployable arms, or separate needles that are inserted into the pelvic tumor. The method further includes delivering energy through the ablation device to the pelvic tumor to ablate the tumor. The method uses RF energy, however, other forms of energy, such as microwave, light (e.g., laser), or acoustic (e.g., ultrasound) energy may also be used to ablate the pelvic tumors.

In accordance with another embodiment of the present invention, a method of treating pelvic tumors includes providing a patient on an operating table, and at least one monitor for a laparoscope and an imaging device, with the at least one monitor located across the operating table from a surgeon and proximate the patient's waist. The at least one monitor may be mounted on a tower located proximate the patient's waist. An energy source and the imaging device are provided adjacent to the at least one monitor, with the energy source and imaging device being located proximate the patient's knees. The method further includes inserting an ablation device into a pelvic region of the patient and positioning the device proximate a pelvic tumor. The location and placement of the ablation device with respect to the pelvic tumor is confirmed using the laparoscope and the imaging device. The method also includes delivering energy to the pelvic tumor to ablate the tumor. The tumor may be maintained at a temperature in the range of approximately 65° C. and 100° C. for at least 7 minutes to ablate the tumor.

In accordance with still another embodiment of the present invention, a surgical system for treating pelvic tumors in a patient lying on an operating table includes an ablation device, an energy source, a laparoscope, and an imaging device. The energy source is coupled to the ablation device and provides energy to the device to ablate a pelvic tumor. The laparoscope and the imaging device are connected to at least one monitor. The at least one monitor is located across the operating table from a surgeon and proximate the patient's waist, while the energy source and imaging device are located alongside the at least one monitor and proximate the patient's knees.

The present invention procedure may be performed by laparoscopy (i.e., open abdominal incision), percutaneously, or hysteroscopically. The Halt procedure has most often utilized conventional laparoscopy with the additional placement of (1) a supra-pubic port or sleeve (10 mm) at the top of the uterus for an intra-abdominal ultrasound probe and (2) an ablation device, also usually in the lower abdominal region. The Halt procedure has also been performed by a trans-abdominal technique, utilizing conventional trans-abdominal ultrasound and placement of the ablation device trans-abdominally with laparoscopic confirmation, as well as by a trans-cervical technique.

DETAILED DESCRIPTION OF THE INVENTION

Figure 1:
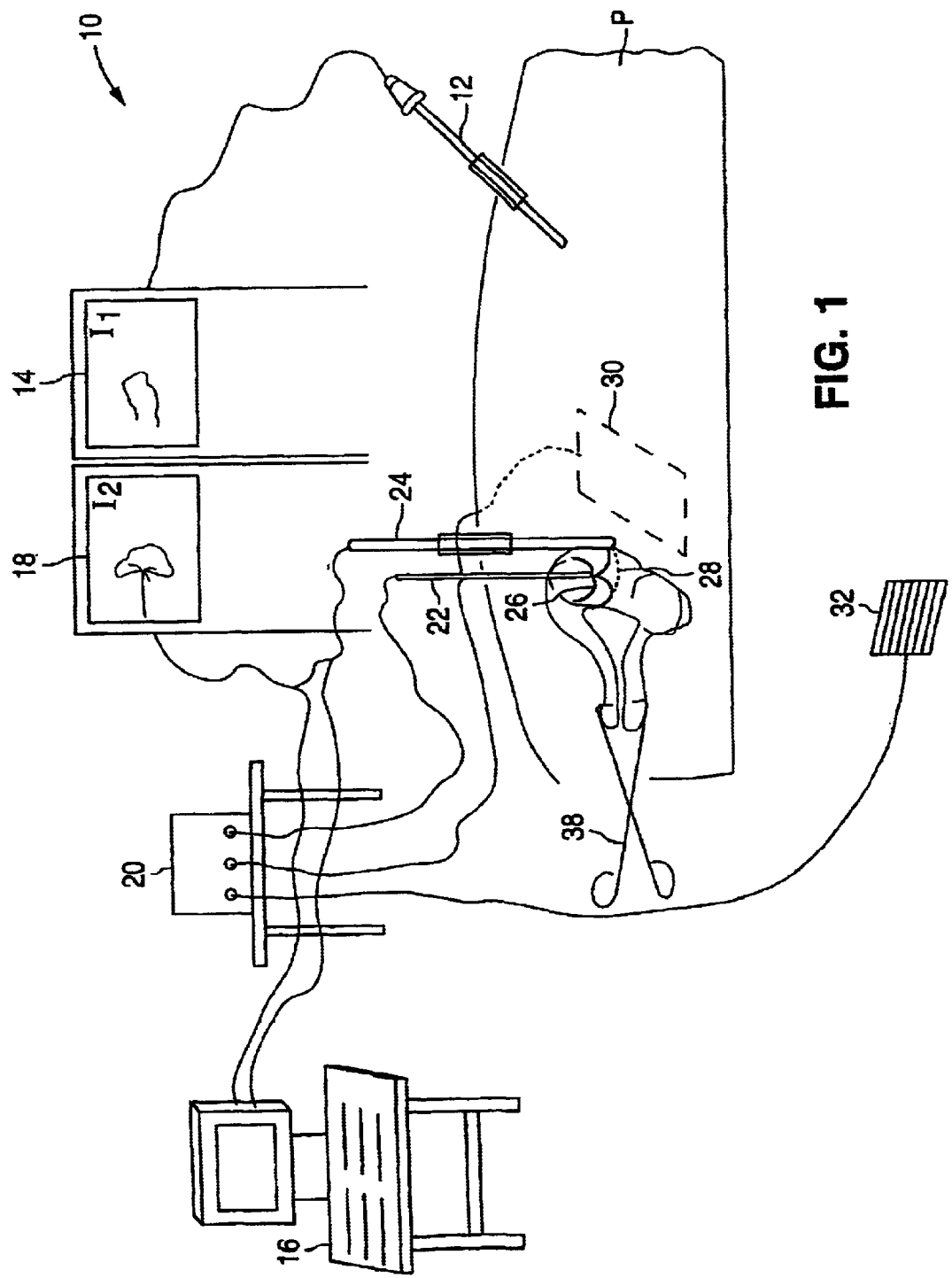
FIG. 1 is a perspective diagram of a surgical system for ablating pelvic tumors, in accordance with the present invention.

Referring first to FIG. 1, a surgical system 10 for ablating pelvic tumors includes a laparoscope 12, a video monitor 14 associated with laparoscope 12, an imaging device 16, a video monitor 18 associated with imaging device 16, an energy source 20 and an ablation device 22. Laparoscope 12, which is inserted into a patient P, is electrically connected to video monitor 14, which displays an image from laparoscope 12. As will be explained in greater detail below, laparoscope 12 enables a surgeon to view the insertion and placement of ablation device 22 into a pelvic region of the patient.

Imaging device 16 is electrically connected to video monitor 18 and provides images of the patient's pelvic region. These images, which are displayed on video monitor 18, enable the surgeon to determine the presence and location of any pelvic tumors. Imaging device 16 shown in FIG. 1 is an ultrasound machine, and includes an intra-abdominal ultrasound probe 24. Instead of intra-abdominal ultrasound probe 24, a transducer (not shown) may be coupled to the ultrasound machine for trans-abdominal ultrasound imaging. In addition, other imaging devices, such as an MRI machine or a CT device, may also be used instead of an ultrasound machine.

Ablation device 22 is a sterile, electrosurgical device that may include a plurality of retractable arms 26. FIG. 1 shows arms 26 of ablation device 22 deployed in a pelvic tumor 28. Examples of the ablation device include the Model 30 Electrosurgical Device and the RITA® StarBurst™ XL, both available from RITA Medical Systems, Inc. Each arm 26 of ablation device 22 is a retractable curved electrode for delivering energy and has a thermocouple (not shown) located at the distal end. Although FIG. 1 shows ablation device 22 as including deployable arms, an ablation device without any arms may also be used. Alternatively, the ablation device may include two or more needles that may be inserted into the tumor.

Ablation device 22 is coupled to energy source 20, which supplies energy to each of the arms 26 of ablation device 22. Energy source 20 may be an RF generator, such as the Model 500 Generator or the RITA® Model 1500 RF Generator, both available from RITA Medical Systems, Inc. The supply of RF energy from energy source 20 to ablation device 22 and to a dispersive electrode 30 is controlled by an operator control, such as by a foot pedal 32. The application of RF energy causes an increase in tumor temperature. At sufficiently high temperatures, cell death occurs, thereby destroying the tumor.

Energy source 20 may further include a mono-polar or bipolar energy source, which allows the ablation device 22 to utilize traditional mono-polar or bipolar cautery to treat very small, superficial tumors and to ablate the track formed during insertion of ablation device 22. Cauterizing the ablation device track reduces or prevents bleeding upon withdrawal of ablation device 22 from the patient.

Figure 2:
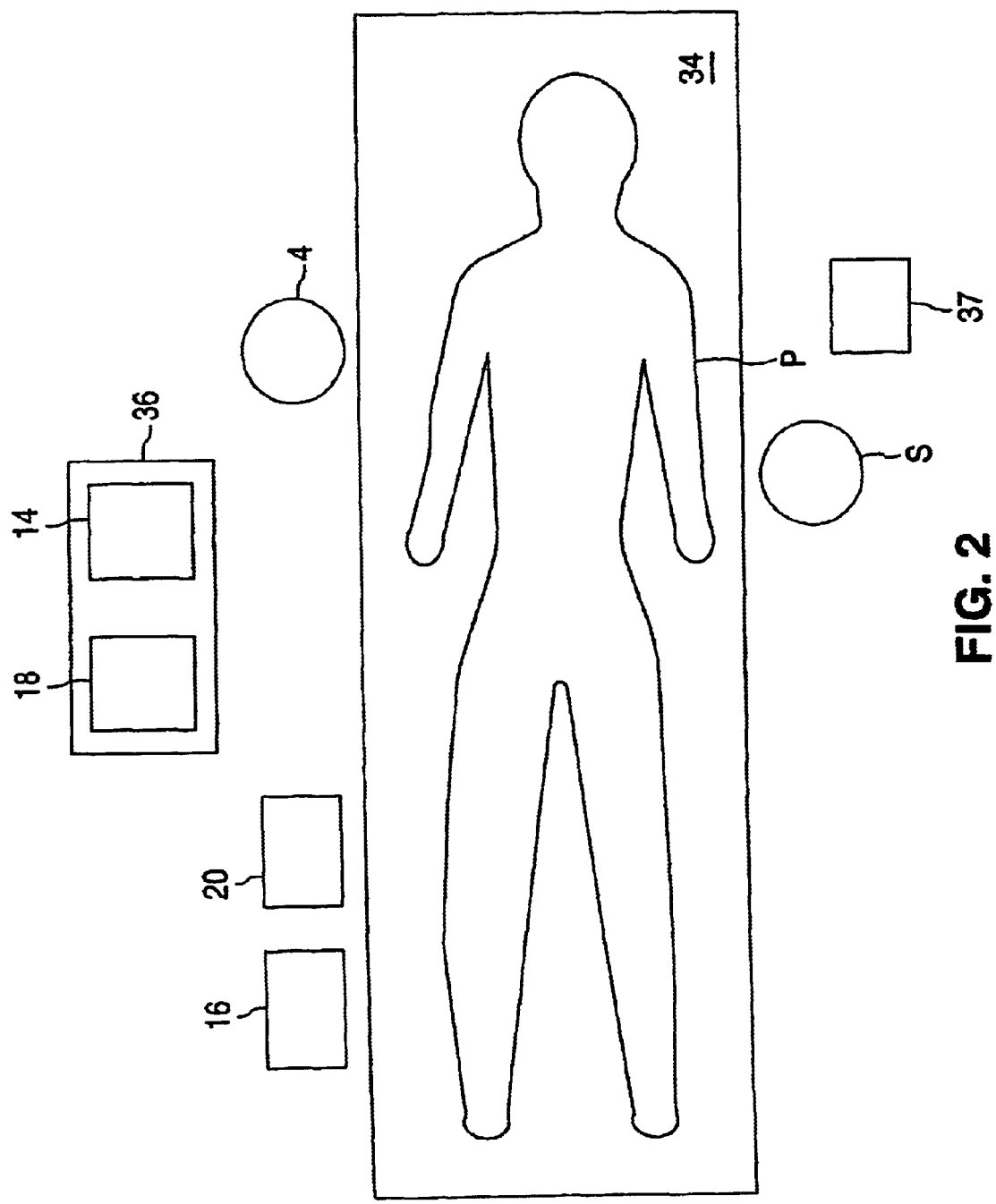
FIG. 2 is a top plan view of the surgical system of FIG. 1, illustrating an arrangement of certain equipment with respect to a patient lying on an operating table.

As better illustrated in FIG. 2, in accordance with the present invention, the equipment of surgical system 10 is set up about the patient in a non-traditional arrangement. FIG. 2 illustrates the patient P lying in a dorsal position on an operating table 34. A tower 36, which supports video monitor 14 for laparoscope 12 and imaging device monitor 18, is located proximate the patient's waist, rather than at the foot of operating table 34. Since the surgeon S is located on the other side of operating table 34 across from tower 36, the surgeon S has a direct view of the monitors 14 and 18. Video monitors 14 and 18 need not be provided on tower 36; they may be suspended from the ceiling and located on the other side of operating table 34 across from the surgeon S. During longer surgical procedures, the placement of video monitors 14 and 18 directly across from the surgeon is more comfortable for the surgeon, as the surgeon need not turn his/her head toward the foot of operating table 34 to view monitors 14 and 18.

Although FIGS. 1 and 2 show separate video monitors 14 and 18 for laparoscope 12 and imaging device 16, respectively, a single monitor capable of simultaneously displaying multiple images from the laparoscope and the imaging device, such as a picture-in-picture monitor, may also be used. The single monitor would be located across the table from the surgeon S and may be mounted on tower similar to tower 36, suspended from the ceiling, or otherwise located across the patient from the surgeon for easy viewing by the surgeon.

Tower 36 may include additional equipment (not shown), such as an insufflation machine, a printer, and a light source. Tower 36 may be provided with wheels so that it may be easily moved about the operating room. An additional monitor 37 for laparoscope 12 may also be provided across from a surgical assistant A, who is seated across the table from the surgeon S, at approximately the patient's chest level. Thus, additional monitor 37 would be located adjacent the surgeon S. Additional monitor 37 may mounted on a movable tower (not shown), suspended from the ceiling, or otherwise appropriately located.

Imaging device 16 and energy source 20, which are not located on tower 36, are positioned along operating table 34, across from the surgeon S, and toward the foot of operating table 34. For example, imaging device 16 and energy source 20 may be located proximate the patient's knees.

Figure 3:
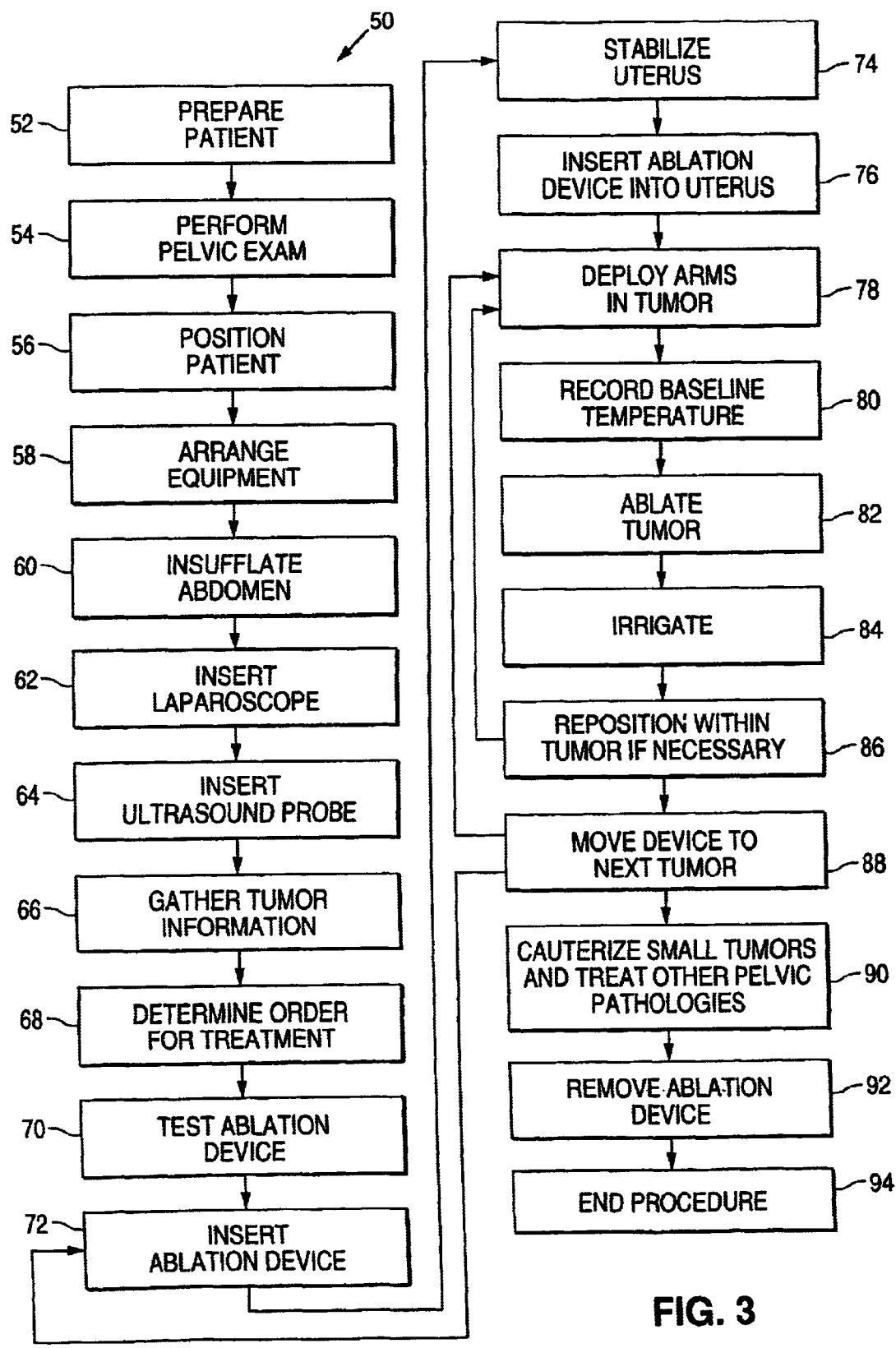
FIG. 3 is a flowchart illustrating a closed laparotomy method of ablating pelvic tumors in accordance with the present invention.

A method of treating pelvic tumors, in accordance with one embodiment of the present invention, will now be described, with reference to the flow chart illustrated in FIG. 3. This method 50 employs a laparoscopic technique for ablating pelvic tumors. First, at step 52, the patient is prepared for laparoscopy by placing and properly adhering dispersive electrode 30 to the lower back of the patient. At step 54, the patient is then placed under general anesthesia, and the surgeon performs an examination of the pelvic region. A manipulator 38 (FIG. 1), such as a tenaculum, is placed on the patient's cervix, and a 14 french foley catheter is inserted into the patient's bladder for emptying the bladder during the surgical procedure.

At step 56, the patient is placed in a dorsal position with her arms at her sides, rather than extended out as an airplane, and a blanket and a surgical drape are placed over the patient. This position provides the surgeon and surgical assistant with more room to move about. The dorsal position is also a safer position for the patient than a frog-leg or lithotomy position, as the dorsal position reduces the instance of nerve injuries and provides better circulation. In addition, the dorsal position does not require the use of custom drapes and stirrups. The surgical drape contains pouches for at least one laparoscopic cord. Serial compression devices (not shown) are placed on the patient's legs to improve circulation during the surgical procedure and reduce the possibility of thromboembolism. In addition, the patient may be placed in a bear hugger system (not shown) to maintain the patient's body temperature while under general anesthesia.

At step 58, the equipment is arranged about operating table 34. As illustrated in FIG. 2, tower 36, which includes video monitors 14 and 18, an insufflation machine, a printer and a light source, is placed proximate the patient's waist and across from the surgeon S. The surgical assistant A is seated across the table from the surgeon at about the patient's chest level, with tower 34 located behind the assistant and further toward the foot of operating table 34. Imaging device 16 and energy source 20 are situated alongside operating table 34 on the same side as the assistant A and toward the foot of operating table 34. The additional monitor 37 is positioned across from the surgical assistant A at about the patient's chest level.

At step 60, the patient P is placed in a trendelenburg position. The surgeon then makes an infra-umbilical or sub-umbilical incision. A verres needle is then inserted into the incision and into the peritoneal cavity. The insufflation machine is then used to insufflate the abdomen with carbon dioxide gas until the abdominal pressure is approximately 15 mm Hg.

Next, at step 62, a 5 mm trocar and sleeve are inserted through the infra-umbilical or sub-umbilical incision. The trocar is then removed and laparoscope 12 is inserted into the sleeve. Laparosope 12 and monitor 14 are then used to verify correct placement of laparoscope 12 within the peritoneal cavity and the absence of any trauma. The sleeve is attached to the carbon dioxide gas supply and includes a valve for controlling the abdominal pressure of the peritoneal cavity.

Steps 60 and 62 discussed above describe a closed laparoscopy procedure. For those patients, for whom the surgeon feels an open laparoscopy would be advantageous, the surgeon would make an infra- or sub-umbilical incision and use a combination of blunt and sharp dissection through subcutaneous tissue. The surgeon would then retract the instruments for exposure. When the fascia is visualized, it is grasped with one or more clamps, elevated and incised. This provides a view of the peritoneum below, which may be bluntly or sharply incised. An appropriate laparoscopic sleeve is then placed, and the abdomen is insufflated with carbon dioxide gas. The laparoscope is then inserted into the sleeve.

At step 64, the surgeon then uses laparoscope 12, while palpating a top of the uterine fundus, to determine an optimal location for an intra-abdominal ultrasound probe. The optimal location is generally at the top of the uterus, rather than supra-pubic. An incision is then made at this location and a 10 mm trocar and sleeve are inserted. The trocar is removed and ultrasound probe 24 is inserted into the sleeve. By way of example, the ultrasound probe 24 may be an Aloka model no. UST-5526L-7.5 probe for use with an Aloka model no. SSDI40U ultrasound machine. Ultrasound probe 24 transmits an image of the pelvic region to ultrasound machine 16. The image is displayed on ultrasound video monitor 18, which is located on tower 36 proximate video monitor 14 for laparoscope 12. Thus, the surgeon may simultaneously view the images on video monitors 14 and 18. As discussed above, a single monitor that simultaneously displays images from laparoscope 12 and imaging device 16 may be used instead of separate monitors 14 and 18.

At step 66, the surgeon examines the entire pelvis and abdomen to confirm the presence or absence of any pathologies. The surgeon also uses laparoscope 12 and ultrasound probe 24 to visualize any tumors, such as uterine leiomyomata. In particular, the surgeon takes note of the number of tumors, and the location and size of each, and compares that information with previously acquired data.

At step 68, the surgeon determines an order for treating the tumors. This order is determined based on the locations of the various tumors, and whether or not the tumors are accessible from a single midline location or require different locations from which to access the tumors. For example, if two tumors are generally along the same track of ablation device 22, the surgeon will first ablate the deeper tumor and, upon retraction of ablation device 22, ablate the remaining tumor. In addition, the surgeon may choose to ablate first a portion of the tumor that is furthest away from the vasculature and work toward the vasculature, or vice versa.

At step 70, the surgeon tests ablation device 22 to ensure that it is operating properly. Ablation device 22 is connected to generator 20, and proper feedback from the thermocouples, if any, is observed. In particular, the surgeon operates foot pedal 32, or any other appropriate operator control, to activate the supply of RF energy from generator 20 and notes an appropriate rise in temperature and any peaks.

At step 72, if the surgeon decides that all of the tumors are approachable via a single midline location, the surgeon makes an incision, approximately 2.5 to 3.0 mm long, and inserts ablation device 22. Entry of ablation device 22 is observed using laparoscope 12. The surgeon uses ultrasound probe 24 to visualize the size and location of the tumors with respect to ablation device 22.

Next, at step 74, the surgeon manipulates the patient's uterus using other techniques to stabilize the uterus.

At step 76, after the surgeon has stabilized the uterus and located the tumors, the surgeon guides ablation device 22 into the uterus and into a wall of the uterus. The surgeon may guide ablation device 22 by changing the position of the uterus relative to ablation device 22. In addition, the surgeon may rotate the ablation device for better penetration of the uterine wall with less movement of the uterus. Ablation device 22 has a plurality of markings (not shown) that enable the surgeon to note the depth of penetration of device 22. Confirmation of the location and placement of ablation device 22 are provided by both laparoscope 12 and ultrasound probe 24.

Next, at step 78, the surgeon advances the tip of ablation device 22 to an appropriate depth for treating a tumor. In doing so, the needle makes only a very small puncture. For example, an ablation device having a needle of 16 gauge may produce a puncture site of approximately 1 mm to 2 mm in diameter. The appropriate depth depends on the size of the tumor. When ablation device 22 has been inserted to the appropriate depth, arms 26 of ablation device 22 are deployed to the appropriate extent in the tumor 28, as illustrated in FIG. 1. A 30° scope is used to ensure that all of the arms 26 remain within the confines of the tumor and do not extend outside of the organ. Arms 26 may effectively anchor ablation device 22 in tumor 28.

At step 80, the surgeon then records a baseline starting temperature of the tumor. The temperature of the tumor is obtained by the thermocouples located at the distal ends of arms 26 of ablation device 22.

At step 82, the surgeon then ablates the tumor by supplying RF energy from generator 20 to ablation device 22. While generator 20 is activated, it is important to monitor the temperature or impedance of all parts of the ablation device. If the temperature or impedance for any part of ablation device 22 is abnormal, it could indicate that that part of the device is external to the organ.

RF energy is supplied to the tumor to raise the temperature of the tumor, such that it is in the range of between approximately 65° C. and 100° C., for about 14 minutes. Cell death occurs at a temperature of about 65° C. However, since these tumors are heterogeneous and, therefore, can differ in density, vasculature and content, a preferred target temperature range for ablating pelvic tumors is between 85° C. and 100° C. For small tumors the target time may be between approximately 7 minutes and 14 minutes. One of ordinary skill in the art, however, will appreciate that ablation times of less than 7 minutes may also be adequate.

The temperature of the tumor, as provided by the thermocouples, is monitored and recorded at least at a 7 minutes and a 14 minutes interval. Thus, at least a baseline starting temperature, half-time temperature, and end-of-ablation-period temperature are recorded for each tumor. While RF energy is being delivered to the tumor, the surgeon keeps an eye on the monitors 14 and 18 to ensure that none of the arms 26 of ablation device 22 inadvertently extends through the tumor. The uterus can contract as it is heated, causing arms 26 of ablation device 22 to project from the tumor and contact normal tissue, which may be damaged by the RF energy. When the tumor has been sufficiently ablated, energy source 20 is turned off.

After each ablation, at step 84 the uterus is irrigated with fluid. The fluid prevents the serosa from drying out as a result of the carbon dioxide gas that is pumped into the abdomen.

If the tumor is larger than the ablation field for the given ablation device, then at step 86, the surgeon may need to reposition ablation device 22 within another part of the tumor and reapply RF energy, repeating steps 76 through 84. Thus, if the tumors are greater in size than the ablation capacity of ablation device 22, multiple applications of energy, of overlapping ablation areas, may be necessary to ablate the bulk of the tumor. For tumors less than 3 cm, however, a single application of the RF energy should be sufficient to ablate the tumor.

At step 88, the surgeon then repositions ablation device 22 at the next tumor. The surgeon may leave ablation device 22 in the same track, if the next tumor is along the same line of approach. The surgeon would retract arms 26 and advance or withdraw ablation device 22 as needed for entry into another tumor. The surgeon would then repeat the ablation sequence of step 76 through step 86 described above.

If the subsequent tumor is in a different location, the surgeon may retract arms 26 of ablation device 22 and withdraw ablation device 22, while applying a mono-polar cautery to reduce or prevent bleeding from the ablation device track. Alternatively, rather than completely withdraw ablation device 22 and re-insert ablation device 22 through another incision, repeating steps 72 through 86, the surgeon may withdraw ablation device 22 until it is only 0.5 cm to 1 cm deep and adjust the uterus until the desired angle of approach is obtained and properly locating ablation device 22 with ultrasound probe 24 or applying traction or pushing inward with uterine manipulator 38.

Small, superficial, subserosal fibroids (e.g., less than 1 cm) may be ablated with a mono-polar cautery at step 90. Bipolar paddles may also be used if the fibroid extends from the wall of the uterus. Similarly, if the tumor is pedunculated, the surgeon may treat or incise the stalk. Mono-polar or bipolar cautery may be applied to subserosal, intramural, and submucuos leiomyomata. In addition, other pelvic pathologies are treated as appropriate.

After all of the tumors have been ablated, at step 92, the surgeon confirms hemostasis, withdraws ablation device 22, and applies a mono-polar cautery with ablation device 22 to the puncture sites, if necessary. A small amount of irrigation fluid may be left in the pelvis.

Finally, at step 94, documentation, including videotapes, ultrasound photographs, and photographs from the laparoscope are obtained. The sleeves are opened to allow the escape of the carbon dioxide gas. The patient is then removed from the trendelenburg position, and a local anesthetic agent is injected into the incisions. The surgeon then repairs the fascia of the 10 mm incision using an absorbable suture, S-retractors to facilitate visualization of the fascial edges. Alis™ clamps are used to facilitate grasping for elevating the fascial edges for suturing, re-approximating the subcutaneous tissue with sutures, closing the skin, and placing Steristrip™ bandages. The surgeon then removes the dispersive electrode 30 and examines the surrounding skin.

The patient is transported to a recovery room, where she will remain until she is tolerating liquids, ambulating with assistance, and voiding adequately.

If the patient's uterus is very large (e.g., 16 weeks or greater), the above-described laparoscopic technique may be less effective. Accordingly, a direct trans-abdominal insertion of ablation device 22 is performed with laparoscopic confirmation only (e.g., no intra-abdominal ultrasound confirmation). In this method the patient is prepared in the same manner as that described above at step 52. The surgeon also performs a pelvic examination, positions the patient, arranges the equipment, forms an infra-umbilical incision, insufflates the patient's abdomen, and inserts laparoscope 12, as in step 54 through to step 62 above. Specifically, the surgeon inspects the abdomen and documents the presence or absence of bowel adhesions or other pathologic conditions that would render this method inappropriate.

Next, the surgeon releases the gas from the patient's abdomen, allowing the abdominal wall to contact an anterior portion of the uterus. A sterile cover drape over a transducer allows for trans-abdominal ultrasound imaging using a non-sterile transducer (not shown). The ultrasound is used to locate and measure the tumors.

The surgeon then makes an incision for ablation device 22 and inserts ablation device 22, using abdominal ultrasonography to guide its insertion. Ablation device 22 may be inserted percutaneously, or trans-abdominally, into the tumor in the uterus.

Ablation device 22 is positioned at a tumor and arms 26 are deployed in the tumor, just as described above with respect to the laparoscopic method. Prior to applying RF energy to the tumor, the surgeon insufflates the abdomen and performs a laparoscopy to confirm that none of the arms 26 of ablation device 22 extend beyond the uterine tissue.

The surgeon then applies RF energy to the tumor, in the same manner as described at step 80 through step 84 above, including recording the baseline, half-time, and end-of-ablation-period temperatures. The surgeon may use the same approach as described above to ablate multiple pelvic tumors. Upon withdrawal of the ablation device 22, the surgeon fulgurates the ablation device track with a monopolar cautery. Thus, remaining steps are the same as step 86 through step 94 described above.

The above-described methods enable the surgeon to ablate substantially all of a tumor from a single, ablation device puncture site. In addition, depending on the location of the tumors, multiple tumors may be ablated from a puncture site. The methods further enable the surgeon to treat all sizes of tumors in any area of the pelvic region.

The foregoing description of the preferred embodiments of the present invention have been provided for illustrative purposes only. They are not intended to be exhaustive or to limit the invention to the precise forms disclosed. Various modifications may be made without departing from the spirit and scope of the inventions as set forth in the appended claims. For example, although the present invention has been described with respect to the treatment of uterine leiomyomata, the present invention may also be used to treat other pelvic tumors, such as those present in the ovaries. The present invention may be performed using a trans-cervical technique or a hysteroscopic technique, in addition to the laparoscopic and trans-abdominal techniques described above. The scope of the invention is defined by the following claims.

What is claimed is:

1. A meted of treating a pelvic tumor comprising:

inserting a tip of an ablation device into a pelvic region, wherein the ablation device includes three or more electrodes deployable from the tip;

deploying the three or more electrodes within a pelvic tumor to avoid contact with normal tissue outside of the pelvic tumor;

confining placement of the three or more electrodes completely within the pelvic tumor with a leroscope and an imaging device including an intra-abdominal ultrasound probe separate from the ablation device; and delivering energy through the three or more electrodes to the pelvic tumor to ablate the tumor.

2. The method of claim 1, wherein inserting the ablation device includes inserting the ablation device into a uterus.

3. The method of claim 2, wherein the ablation device is inserted through an abdomen and into the uterus.

4. The method of claim 2, wherein the ablation device is inserted through a cervix and into the uterus.

5. The method of claim 1, wherein the ablation device includes a plurality of deployable arms and further comprising deploying the plurality of arms completely within the pelvic tumor.

6. The method of claim 5, further comprising inserting the ultrasound probe into an incision proximate a top of a uterus.

7. The method of claim 1, wherein the Imaging device is an ultrasound machine.

8. The method of claim 1, wherein delivering energy includes delivering RF energy to the pelvic tumor.

9. The method of claim 1, wherein delivering energy includes heating the pelvic tumor to a temperature between approximately 65° C. and approximately 100° C. for at least 7 minutes.

10. The method of claim 9, wherein the pelvic tumor is maintained at the temperature for between approximately 7 and approximately 14 minutes.

11. The method of claim 10, further comprising:

repositioning the ablation device proximate a second pelvic tumor;

confirming placement of the ablation device; and delivering energy to the second pelvic tumor to ablate the second tumor.

12. The method of claim 11, wherein the second pelvic tumor is located closer to a vasculature than a first pelvic tumor.

13. A method of treating pelvic tumors comprising:

providing a patient on an operating table;

providing at least one monitor for a laparoscope and an imaging device including an intra-abdominal ultrasound probe, the at least one monitor being located across the operating table from a surgeon and proximate the patient's waist;

providing an energy source and the imaging device adjacent to the at least one monitor, the energy source and the imaging device being located proximate the patient's knees;

inserting a tip of an ablation device into a pelvic region of the patient, wherein the ablation device includes three or more electrodes deployable from the tip, and further wherein the ablation device is separate from the intra-abdominal ultrasound probe;

deploying the three or more electrodes within a pelvic tumor to avoid contact with normal tissue outside of the pelvic tumor;

confirming placement of the three or more electrodes completely within the pelvic tumor with the laparoscope and the imaging device; and delivering energy through the tree or more electrodes to the pelvic tumor to ablate the tumor.

14. The method of claim 13, wherein the patient is in a dorsal position on the operating table.

15. The method of claim 13, wherein inserting the ablation device includes inserting the ablation device through an abdomen and into a uterus.

16. The method of claim 15, further comprising repositioning the uterus relative to the ablation device.

17. The method of claim 15, further comprising rotating the ablation device during insertion to reduce movement of the uterus.

18. The method of claim 15, further comprising inserting an ultrasound probe into an incision proximate a top of the uterus.

19. The method of claim 13, wherein inserting the ablation device includes inserting the ablation device through a cervix and into a uterus.

20. The method of claim 13, wherein the ablation device includes a plurality of deployable arms and further comprising deploying the plurality of arms of the ablation device completely within the pelvic tumor.

21. The method of claim 13, wherein the imaging device is an ultrasound machine.

22. The method of claim 13, wherein delivering energy includes delivering RF energy to the pelvic tumor.

23. The method of claim 13, wherein delivering energy includes heating the pelvic tumor to a temperature between approximately 65° C. and approximately 100° C. for at least 7 minutes.

24. The method of claim 13, further comprising removing the ablation device from the pelvic region, including cauterizing a track of the ablation device.

25. A method of treating pelvic tumors comprising:

inserting a tip of an ablation device including three or more electrodes deployable from the tip into a single puncture site in a pelvic region, the puncture site being approximately 1 mm to 2 mm in diameter;

deploying the three or more electrodes within at least one pelvic tumor to avoid contact with normal tissue outside of the at least one pelvic tumor, the at least one pelvic tumor having a diameter of at least 1 cm;

confirming placement of the three or more electrodes completely within the at least one pelvic tumor with a laparoscope and an imaging device including an intra-abdominal ultrasound probe separate from the ablation device;

delivering RF energy to the ablation device; and heating the at least one pelvic tumor to a temperature between approximately 85° C. and approximately 100° C. for between approximately 7 and 14 minutes, wherein from the single puncture site substantially all of the at least one pelvic tumor is ablated.

26. The method of claim 25, wherein the pelvic tumor is a uterine fibroid.

27. The method of claim 26, further comprising:

repositioning the ablation device proximate a second pelvic tumor from the single puncture site;

confirming placement of the ablation device; and delivering energy to the second pelvic tumor to ablate the second tumor.

28. A method of treating a uterine fibroid comprising:

manipulating a uterus with an intra-abdominal ultrasound probe to position and stabilize the uterus, wherein the uterus has at least one uterine fibroid;

inserting a tip of an ablation device into the uterus, wherein the ablation device includes at least three electrodes deployable from the tip;

deploying the at least three electrodes within the uterine fibroid to avoid contact with normal tissue outside of the uterine fibroid;

confirming placement of the at least three electrodes completely within the uterine fibroid with a laparoscope and the intra-abdominal ultrasound probe; and delivering energy through the at least three electrodes to the uterine fibroid to ablate the fibroid.

* * * * *